United States Patent
Vairavan et al.

(10) Patent No.: US 9,959,390 B2
(45) Date of Patent: May 1, 2018

(54) MODELING TECHNIQUES FOR PREDICTING MORTALITY IN INTENSIVE CARE UNITS

(71) Applicant: KONINKLIJKE PHILIPS N.V., Eindhoven (NL)

(72) Inventors: Srinivasan Vairavan, Ossining, NY (US); Larry James Eshelman, Ossining, NY (US); Adam Jacob Seiver, Los Altos Hills, CA (US); Abigail Acton Flower, Mahopac, NY (US); Syed Waseem Haider, Somers, NY (US)

(73) Assignee: Koninklijke Philips N.V., Eindhoven (NL)

( * ) Notice: Subject to any disclaimer, the term of this patent is extended or adjusted under 35 U.S.C. 154(b) by 473 days.

(21) Appl. No.: 14/421,455

(22) PCT Filed: Aug. 30, 2013

(86) PCT No.: PCT/IB2013/058166
§ 371 (c)(1),
(2) Date: Feb. 13, 2015

(87) PCT Pub. No.: WO2014/033681
PCT Pub. Date: Mar. 6, 2014

(65) Prior Publication Data
US 2015/0213227 A1 Jul. 30, 2015

Related U.S. Application Data

(60) Provisional application No. 61/695,586, filed on Aug. 31, 2012.

(51) Int. Cl.
*G06N 99/00* (2010.01)
*G06F 19/00* (2011.01)
*G06N 7/00* (2006.01)

(52) U.S. Cl.
CPC ........ *G06F 19/3437* (2013.01); *G06F 19/345* (2013.01); *G06F 19/3431* (2013.01); *G06N 7/005* (2013.01); *G06N 99/005* (2013.01)

(58) Field of Classification Search
CPC ............. G06F 19/3437; G06F 19/3431; G06F 19/345; G06N 7/005; G06N 99/005
(Continued)

(56) References Cited

U.S. PATENT DOCUMENTS 7,801,591 B1 * 9/2010 Shusterman ......... A61B 5/0205
600/300
8,244,654 B1 * 8/2012 Hobgood .............. G06F 19/328
600/300

(Continued)

OTHER PUBLICATIONS

Clermont G. et al., "Predicting hospital mortality for patients in the intensive care unit: A comparison of artificial neural networks with logistic regression models", Crit Care Med, 2001, vol. 29, No. 2.*

(Continued)

*Primary Examiner* — Dave Misir

(57) ABSTRACT

A medical modeling system and method predict a risk of a physiological condition, such as mortality, for a patient. Measurements of a plurality of predictive variables for the patient are received. The plurality of predictive variables are predictive of the risk of the physiological condition. The risk of the physiological condition is calculated by applying the received measurements to at least one model modeling the risk of the physiological condition using the plurality of predictive variables. The at least one model includes at least one of a hidden Markov model and a logistic regression model. An indication of the risk of the physiological condition is output to a clinician.

13 Claims, 7 Drawing Sheets

(58) Field of Classification Search
USPC .......................................................... 706/12
See application file for complete search history.

(56) References Cited

U.S. PATENT DOCUMENTS

| | | | | |
|---|---|---|---|---|
| 8,417,541 | B1* | 4/2013 | Kramer | G06Q 10/10 |
| | | | | 705/2 |
| 2006/0271407 | A1* | 11/2006 | Rosenfeld | A61B 5/412 |
| | | | | 705/3 |
| 2006/0289020 | A1* | 12/2006 | Tabak | A61B 5/4833 |
| | | | | 128/898 |
| 2009/0275057 | A1 | 11/2009 | Linke et al. | |
| 2010/0057490 | A1* | 3/2010 | Kocis | G06F 19/345 |
| | | | | 705/2 |
| 2010/0256463 | A1* | 10/2010 | Greenwald | A61B 5/0002 |
| | | | | 600/301 |
| 2012/0059779 | A1* | 3/2012 | Syed | G06F 19/3431 |
| | | | | 706/12 |
| 2012/0095300 | A1* | 4/2012 | McNair | A61B 5/021 |
| | | | | 600/300 |
| 2013/0197924 | A1* | 8/2013 | Kocis | G06Q 50/22 |
| | | | | 705/2 |

OTHER PUBLICATIONS

Kim S. et al., "A Comparison of Intensive Care Unit Mortality Prediction Models through the Use of Data Mining Techniques", Healthcare Informatics Research, vol. 17, No. 4, Dec. 2011.*
Vairavan S. et al., "Prediction of Mortality in an Intensive Care Unit using Logistic Regression and a Hidden Markov Model", Computing in Cardiology, 2012. (Date and authors precludes usage).*

* cited by examiner

| Oxygen Transport | Organ Dysfunction other than Liver | Liver Dysfunction | Hematologic | | |
|---|---|---|---|---|---|
| Lactate | Creatinine | Bilirubin | Age | Intensive Care Unit (ICU) Type | |
| Partial Pressure of Carbon Dioxide in the Arterial Blood (PaCO2) | White Blood Count (WBC) | Alanine Aminotransferase (ALT) | | | |
| Systolic Blood Pressure (NiSysABP) | Troponin T | Aspartate Aminotransferase (AST) | | | |
| Diastolic Blood Pressure (NiDiasABP) | Hematocrit (HCT) | | | | |
| Heart Rate (HR) | Daily Urine Output | | | | |
| Respiratory Rate | Magnesium (Mg) | | | | |
| Oxygen Saturation (SaO2) | Sodium (Na) | | | | |
| Ratio of Partial Pressure of Oxygen in Arterial Blood (PaO2) to fraction of Inspired Oxygen (FiO2) (PFratio) | Glucose | | | | |
| pH | Glasgow Coma Scale (GCS) | | | | |

FIG. 3

| Model | Performance Metrics | |
|---|---|---|
| | AUC | Min(Sen., PPV) |
| HMM | 0.839 | 0.504 |
| SAPS-I Model | 0.660 | 0.317 |

| Model | Performance Metrics | | |
|---|---|---|---|
| | AUC | Min(Sen., PPV) | H-Statistic |
| LogR Model | 0.850 | 0.520 | 26.90 |
| SAPS-I Model | 0.660 | 0.317 | 66.04 |

MODELING TECHNIQUES FOR PREDICTING MORTALITY IN INTENSIVE CARE UNITS

CROSS-REFERENCE TO PRIOR APPLICATIONS

This application is the U.S. National Phase application under 35 U.S.C. § 371 of International Application No. PCT/IB2013/058166, filed on Aug. 30, 2013, which claims the benefit of U.S. Provisional Application No. 61/695,586, filed on Aug. 31, 2012. These applications are hereby incorporated by reference herein.

The following relates generally to clinical decision making. It finds particular application in conjunction with predicting mortality in intensive care units (ICUs) and will be described with particular reference thereto. However, it is to be understood that it also finds application in other usage scenarios and is not necessarily limited to the aforementioned application.

Intensive care improvement comes with a price of making ICUs responsible for an increasing percentage of the health care budget. Further, resource availability limitations force ICUs to make sure that intensive care is applied only to those who are likely to benefit from it. Critical decisions include interrupting life-support treatments and issuing do-not-resuscitate orders when intensive care is considered futile. Under this context, mortality assessment is a crucial task, being used not only to predict the final clinical outcome, but also to evaluate the ICU effectiveness.

One way to optimize the utility of ICU care is to identify critically ill patients that are at higher risks of mortality. Since the early 1980s, clinical scores have been developed to assess severity of illness and organ dysfunction in the ICU setting. Indeed, in the context of intensive medicine, severity scores are instruments that aim primarily at stratifying patients based on risk adjustment of clinical condition. Furthermore, severity scores have been used to improve the quality of intensive care and guide local planning of resources.

Known severity scores, such as the simplified acute physiology score (SAPS)-I, are widely used to account for population differences in studies aiming to compare how medications, care guidelines, surgery, and other interventions impact mortality in ICU patients. However, known severity scores are typically not used to determine a patient-specific prediction of in-hospital mortality. Further, known severity scores are typically poor predictors of mortality, do not cover the mortality risk due to development of diseases, such as sepsis and pneumonia, do not include interactions between variables (such as heart rate (HR) and diastolic blood pressure), and depend on patient history. Even more, systems employing known severity scores typically do not provide a continuous mortality risk assessment or display trend information of mortality risk assessment.

The following provides new and improved methods and systems which overcome the above-referenced problems and others.

In accordance with one aspect, a medical modeling system for predicting a risk of a physiological condition for a patient is provided. At least one processor of the medical modeling system is programmed to receive measurements of a plurality of predictive variables for the patient. The plurality of predictive variables are predictive of the risk of the physiological condition. The at least one processor is further programmed to calculate the risk of the physiological condition by applying the received measurements to at least one model modeling the risk of the physiological condition using the plurality of predictive variables. The at least one model includes at least one of a hidden Markov model and a logistic regression model. Even more, the at least one processor is programmed output an indication of the risk of the physiological condition to a clinician.

In accordance with another aspect of the present application, a medical modeling method for predicting a risk of a physiological condition for a patient is provided. Measurements of a plurality of predictive variables for the patient are received. The plurality of predictive variables are predictive of the risk of the physiological condition. The risk of the physiological condition is calculated by applying the received measurements to at least one model modeling the risk of the physiological condition using the plurality of predictive variables. The at least one model includes at least one of a hidden Markov model and a logistic regression model. An indication of the risk of the physiological condition is output to a clinician.

In accordance with another aspect of the present application, a medical system is provided. The medical system includes a medical modeling system for predicting a risk of a physiological condition for a patient. The medical modeling system receives measurements of a plurality of predictive variables for the patient. The plurality of predictive variables are predictive of the risk of the physiological condition. The medical modeling system further calculates the risk of the physiological condition by applying the received measurements to at least one model modeling the risk of the physiological condition using the plurality of predictive variables. The at least one model includes at least one of a hidden Markov model and a logistic regression model. The medical system further includes a clinical decision system (124) receiving the calculated risk of the physiological condition and providing a clinician with clinical decision support based on the calculated risk of the physiological condition.

One advantage resides in improved detection and prediction of mortality.

Another advantage resides in the use of mortality predications to aid intensive care unit (ICU) clinicians in clinical decision making on planning, scheduling and allocating of ICU resources among critically ill patients with varying levels of mortality risks.

Another advantage resides in mortality models that use a wide spectrum of variables for accessing mortality risk due to different organs and diseases, such as sepsis and pneumonia.

Another advantage resides in the use of time-series, measured data from ICU monitors and staff to estimate mortality risk at every measurement or at any other time interval.

Another advantage resides in a model including interactions between variables (e.g., heart rate (HR) and diastolic blood pressure, or partial pressure of oxygen in arterial blood (PaO2) and fraction of inspired oxygen (FiO2)).

Another advantage resides in quantified continuous real-time mortality risk assessment (e.g., on a scale from 0 to 1).

Another advantage resides in trend based alarming for mortality detection.

Another advantage resides in selection of variables and time sequences for assessment of mortality based on the observations and expert knowledge of the ICU clinicians with many years of experience.

Another advantage resides in real-time mortality risk computation for continuous time signals and/or measurements.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 3 illustrates a table of variables used during testing of a mortality HMM.

The present application provides a clinical decision support tool for intensive care unit (ICU) clinicians. The tool aids decision making for critically ill patients by providing a patient-specific prediction of in-hospital mortality. The tool can include a model predicting mortality based on vital signs, lab results, fluids and other relevant data that are commonly available in an ICU. The model can be a logistic regression (log R) model, a hidden Markov model (HMM), or a model combining these two models. The models model a patient's dynamic health status in the face of uncertainty imposed by the pathophysiology of the patient, and other influential factors within the ICU.

Figure 1:
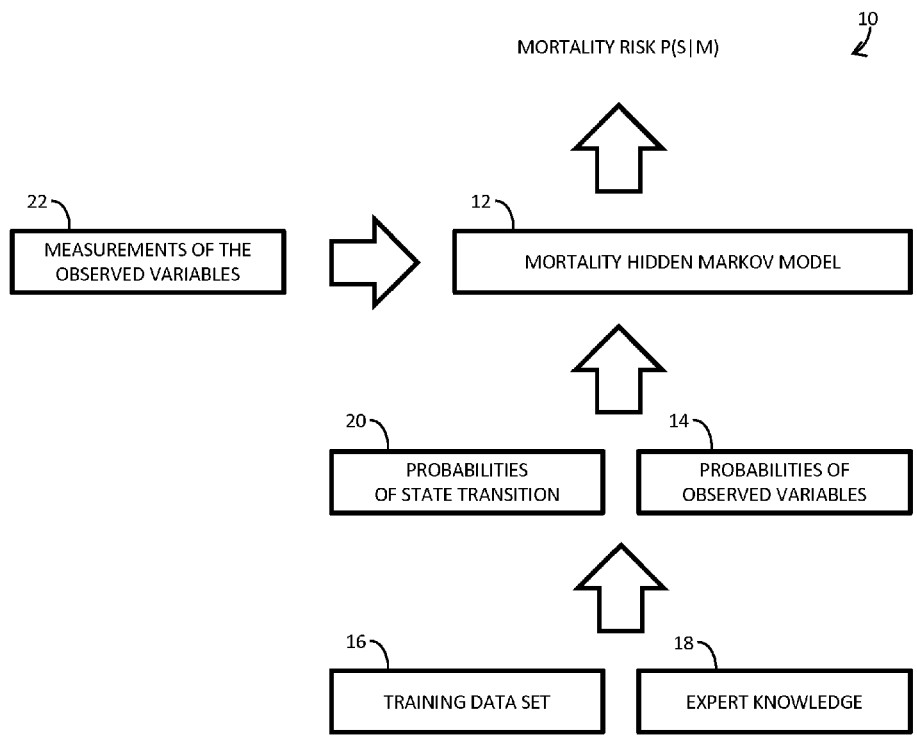
FIG. 1 illustrates the use of a mortality hidden Markov model (HMM).

With reference to FIG. 1, a block diagram 10 illustrates the use of a mortality HMM 12 for predicting patient mortality. HMMs have been used for the last 20 years in speech recognition and academia. HMMs are dynamic models that predict over time. The basic idea of an HMM is to estimate hidden states of a process using observable variables over time. The mortality HMM 12 of the present application infers the trend of a critically ill patient's mortality status (i.e., the hidden state) by observing trends in variables describing the physiological state of the patient over time. These variables can include lab tests (e.g., creatinine, alanine aminotransferase (ALT), etc.), vital signs (e.g., heart rate (HR), blood pressure (BP), etc.), physiological scores (e.g., early warning score (EWS), vital signs instability index (VIX), simplified acute physiology score (SAPS)-I, etc.), fluids, demographics (e.g., age, gender, etc.) and other relevant variables (e.g., ICU type).

The mortality HMM 12 requires three types of probabilities 14 for each observed variable of the mortality HMM 12. These three probability types include: 1) the probability P(V) of an observed variable V over a training population; 2) the probability P(V|A) of an observed variable V for only those patients of the training population who lived to be discharged from the ICU (i.e., are alive A); and 3) the probability P(V|D) of an observed variable V for only those patients of the training populating who died before being discharged from the ICU (i.e., are dead D). The training population can be localized to a patient population to which the patient being assessed by the mortality HMM 12 belongs. For example, the training population can be localized to a patient population sharing a disease or physiological condition with the patient, a patient population corresponding to a medical institution treating the patient, a patient population corresponding to a geographical region (e.g., a country, a state, a city, a county, etc.) of the patient, or a combination of the foregoing patient populations.

The probabilities 14 of the observed variables of the mortality HMM 12 are typically computed from a training data set 16 describing the training population. However, these probabilities 14 can also be determined using clinical knowledge 18 of experts (e.g., clinical guidelines) or any other relevant data. The training data set 16 includes a plurality of records, each corresponding to an ICU patient. The record for an ICU patient includes one or more measurements over time, typically a plurality of measurements over time (i.e., a time series), for each variable of the mortality HMM 12. Typically, the measurements span from admittance to the ICU until the patient dies or is discharged from the ICU, whichever comes first, or until a predetermined period of time (e.g., 48 hours) passes or the patient dies, whichever comes first. Further, the record for a patient includes an indication as to whether the patient died before discharge from the ICU or lived to be discharged from the ICU.

A global competition, PhysioNet/CinC Challenge 2012, made a data set describing eight thousand ICU patients publicly available to develop methods for patient-specific prediction of in-hospital mortality. The data set contains measurements for up to 42 variables for each ICU patient. The variables include general descriptors (e.g., age, gender, height, weight, etc.), vital signs and lab tests. For each patient, each variable includes a single measurement/value (e.g., for a general descriptor) or a time series of measurements spanning from the first ICU stay of the patient for a period of 48 hours (unless the patient died before then) with at least one measurement within the 48 hour period and vital signs and lab tests measured every hour. Further, the data set contains the mortality outcome for half of these ICU patients. While not necessary, the probabilities of the observed variables of the mortality HMM 12 can be computed using the data set provided by PhysioNet/CinC Challenge 2012 as the training data set 16.

In addition to requiring the three types of probabilities 14 for each observed variable of the mortality HMM 12, the mortality HMM 12 requires four state transition probabilities 20: the probability P(AD) that the patient goes from alive to dead; the probability P(DA) that the patient goes from dead to alive (i.e., 0); the probability P(AA) that the patient goes from alive to alive; and the probability P(DD) that the patient goes from dead to dead (i.e., 1). These state transition probabilities 20 can be computed from the training data set 16 describing the training population. Additionally or alternatively, these state transition probabilities 20 can also be determined using clinical knowledge 18 of experts (e.g., clinical guidelines) or other relevant data.

Figure 2:
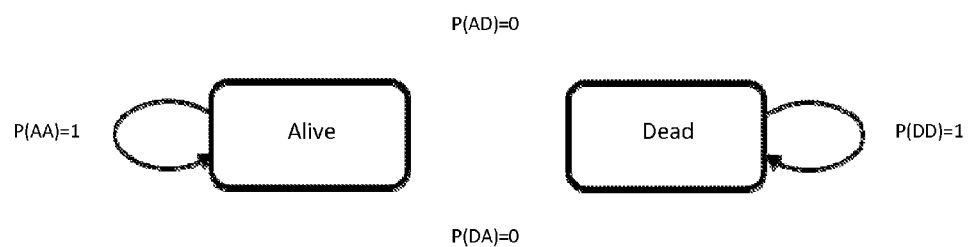
FIG. 2 illustrates the Markov chain (MC) for a mortality HMM.

To define the mortality HMM 12, the mortality state S of the patient to which the mortality HMM 12 is applied is defined as S={A, D}, where A is alive and D is dead. In other words, the mortality state S can be A or D. P(A) is the probability that the patient lives, and P(D)=1−P(A) is the probability that the patient dies (i.e., the mortality risk). FIG. 2 illustrates the Markov chain (MC) for the mortality HMM 12. As illustrated, the MC is a binary state MC, wherein transitions only happens to the state itself (i.e., P(AA)=P(DD)=1 and P(AD)=P(DA)=0). The MC is typically implemented using Viterbi algorithm. The Markovian assumption that current and future measurements and future states depend only on the present mortality state is made. In other words, the current mortality state makes present and future measurements and future states independent of past measurements and states.

During application of the mortality HMM 12, measurements 22 of observed variables from the patient to which the mortality HMM 12 is being applied are provided to the mortality HMM 12, along with the transition probabilities 20 and the probabilities 14 of the observed variables, to compute the final output in terms of mortality risk over a sequence or trend of the patient's mortality state over time. The mortality HMM 12 accommodates n>1 observed variables, each variable being measured in response to an event (e.g., a periodic event (e.g., every 10 minutes), a physiological event (e.g., atrial fibrillation), a clinical event (e.g., check-in to the ICU), etc.). Each time at least one observed variable of the patient is measured, or in response to some other event (e.g., a periodic event, a physiological event, etc.), the mortality HMM 12 updates the prediction of mortality using the most recent measurements M={V1, V2, ..., Vn} of the n observed variables. In that regard, as m measurements of the observed variables over time become available, the trend of mortality risk over time P(D1, D2, ..., Dm|M1, ..., Mm) is quantified.

The observed variables of the mortality HMM 12 are typically selected so that: 1) when a patient's oxygen transport performs poor, measurements at that point in time from the related observed variables raise the mortality risk; 2) subsequently, when the patient goes into organ dysfunction other than liver, the measurements from other related observed variables further raise the mortality risk; and 3) eventually, when the patient goes into liver dysfunction, the risk computed at that point is likely the highest mortality risk. By selecting the observed variables according to this approach, the mortality HMM 12 can infer overall mortality risk from variables targeting oxygen transport in, for example, the first 24 hours that could be a prelude to organ dysfunction other than liver. Organ dysfunction other liver dysfunction is anticipated to follow and variables regarding organ dysfunction other than liver dysfunction are used to evaluate the subsequent risk of organ dysfunction. Further, liver dysfunction is anticipated to follow organ dysfunction other than liver dysfunction and variables for liver dysfunction evaluate the subsequent risk of liver dysfunction. Notwithstanding the foregoing selection scheme, other approaches to selecting the observed variables are contemplated. Further, the selected variables can be specifically selected for the patient to which the mortality HMM 12 is being applied.

When measurements of the observed variables are made so infrequently that only one measurement for each variable is available, the MC of the mortality HMM 12 reduces to a Bayesian inference model, as described by the following equations.

$$P(S \mid M) = P(S \mid V_1, \ldots, V_n) \quad (1)$$

$$P(S \mid V_1, \ldots, V_n) = \frac{P(V_1 \mid S) \ldots P(V_n \mid S) P(S)}{P(V_1) \ldots P(V_n)} \quad (2)$$

The mortality risk computed in the above equations is not based on trend, rather it's a snap shot in time.

To validate the mortality HMM 12, both the mortality HMM 12 and the SAPS-I model were tested using the data provided by PhysioNet/CinC Challenge 2012. A subset of the patient records were selected at random. Patients under the age of 16 and patients whose initial ICU stays were shorter than 48 hours (i.e., approximately the median stay) were excluded from the random selection.

The variables used by the mortality-prediction model 12 are shown in FIG. 3. The variables include lactate, creatinine, bilirubin, age, partial pressure of carbon dioxide in the arterial blood (PaCO2), white blood count (WBC), ALT, ICU type, systolic BP (NISysABP), troponin T, aspartate aminotransferase (AST), diastolic BP (NIDiasABP), hematocrit (HCT), HR, daily urine output, respiratory rate, magnesium (Mg), oxygen saturation (SaO2), sodium (Na), ratio of partial pressure of oxygen in arterial blood (PaO2) to fraction of inspired oxygen (FiO2) (PFratio), glucose, pH, and Glasgow Coma Scale (GCS). The variables were selected such that there is at least one variable for observing each of: oxygen transport, ventilation, and perfusion in the body; organ dysfunction other than liver dysfunction; and liver dysfunction. There are also variables describing demographic information and other variables indicative of the general health of the patient.

Figure 4:
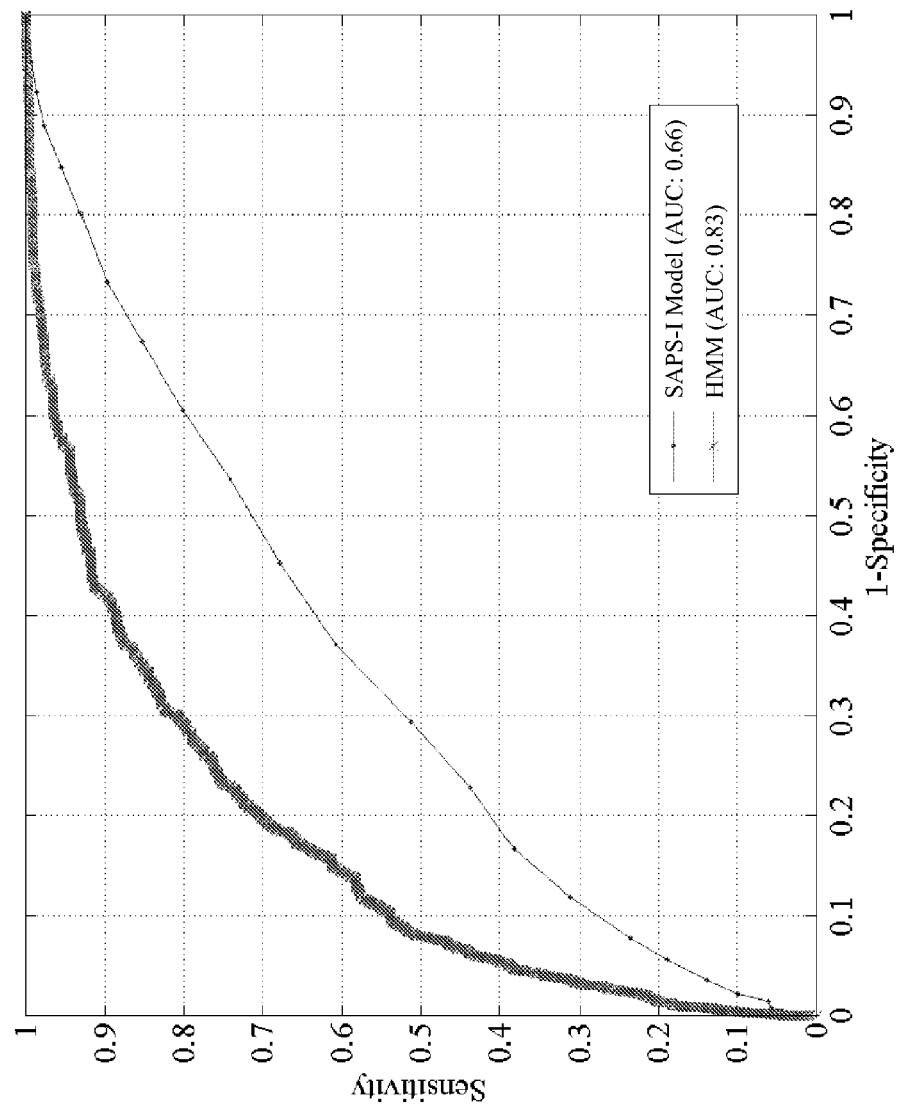
FIG. 4 illustrates receiver operating characteristic (ROC) curves for both a mortality HMM and a simplified acute physiology score (SAPS)-I model.
Figures 5, 6:
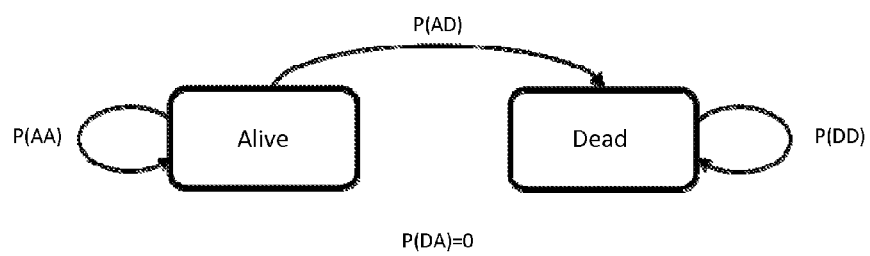
FIG. 5 illustrates a table of both the area under curve (AUC) and the minimum of sensitivity and positive predictive value (PPV) for both a mortality HMM and a SAPS-I model.
FIG. 6 illustrates the Markov chain (MC) for a mortality HMM.

ROC analysis was performed on the selected records using the prediction HMM 12 and the SAPS-I model to assess the detection capability of the mortality HMM 12. In that regard, two metrics, the AUC and the minimum of sensitivity and positive predictive value (PPV), were obtained from the ROC curves to evaluate the detection capability of the mortality HMM 12. With these metrics, the higher the value (i.e., the closer to 1), the better the detection capability. The results of the ROC analysis are shown in FIGS. 4 and 5. FIG. 4 illustrates the ROC curves for both the mortality HMM 12 and the SAPS-I model. FIG. 5 illustrates a table showing both AUC and the minimum of sensitivity and PPV for both the mortality HMM 12 and the SAPS-I model. As can be seen, the AUC of the mortality HMM 12 is 83.9%, whereas the AUC for the SAPS-I model is 66%. Further, the minimum of sensitivity and PPV of the mortality HMM 12 is 50.4%, whereas the minimum of sensitivity and PPV for the SAPS-I model is 31.7%. Hence, the detection capability of the mortality HMM 12 exceeds that of the SAPS-I model.

While the mortality HMM 12 was previously limited to predicting patient mortality, the mortality HMM 12 can be extended to find the best mortality state sequence that defines the trend over time. In this instance, the MC expressed in FIG. 2 is modified to include a transition from the alive state to the dead state. The converse is not physiologically possible. The updated Markov chain (MC) for the mortality HMM 12 is shown in FIG. 6.

This extension to the mortality HMM 12 provides more insight into the changing mortality state of the patient to which the mortality HMM 12 is applied using available measurements. It allows ICU clinicians to better manage and plan ICU resources. In that regard, the prediction of the future state sequence can provide a peek into the potential future outcome, which can aid in the selection interventions. When three measurements are made at different times, ($M_1$, $M_2$, $M_3$), the extension to the mortality HMM 12 provides one of the following state transition sequences for the patient's mortality state: {($A_1$, $A_2$, $A_3$), ($A_1$, $A_2$, $D_3$), ($A_1$, $D_2$, $D_3$), ($D_1$, $D_2$, $D_3$)}. For m measurements at different times, there are m+1 possible state sequences. The extension to the mortality HMM 12 provides the state sequence that best fits the patient's mortality state.

Figures 7, 9:
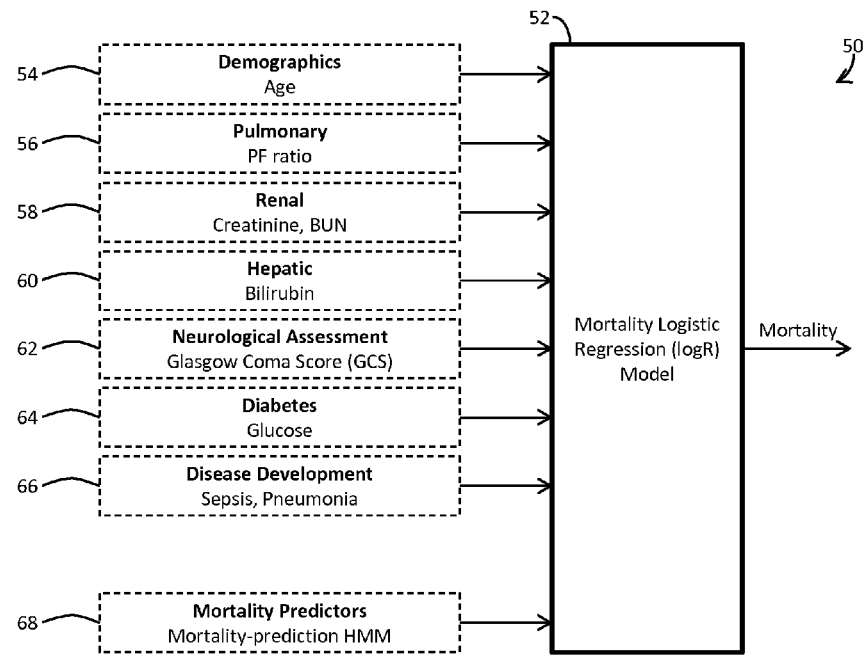
FIG. 7 illustrates the use of a mortality logistics regression (log R) model.
FIG. 9 illustrates a table of both the area under curve (AUC) and the minimum of sensitivity and positive predictive value (PPV) for both a mortality log R model and a SAPS-I model.

With reference to FIG. 7, a block diagram 50 illustrates the use of a mortality logistic regression (log R) model 52 for predicting patient mortality. The mortality log R model 52 uses a nonlinear mapping of n>1 independent or predictor variables x to the dependent or response variable p (e.g., in-hospital mortality or in-hospital survival) through the logistic regression function or log it transformation. The predictor variables can include one or more of lab tests (e.g., creatinine, blood urea nitrogen (BUN), ALT, etc.), vital signs (e.g., HR, BP, etc.), physiological scores (e.g., EWS, VIX, SAPS-I, mortality risk according to the mortality HMM 12, etc.), demographics (e.g., age, gender, etc.) and other relevant predictor variables (e.g., ICU type).

The mortality log R model 52 can be defined as follows:

$$p = \frac{e^{\beta_0 + \beta_1 x_1 + \ldots + \beta_n x_n}}{1 + e^{\beta_0 + \beta_1 x_1 + \ldots + \beta_n x_n}} \quad (3)$$

where p is the probability of mortality or survival, $\beta_0$ is a constant, and $\beta_1 \ldots \beta_n$ are coefficients of the corresponding predictor variables $x_1 \ldots x_n$. $\beta_0 \ldots \beta_n$ are determined by fitting the log R model to a training data set. Namely, a minimization technique, such as the maximum likelihood estimator (MLE), is applied to a likelihood function assessing how well the mortality log R model 52 fits to the training data set to determine $\beta_0 \ldots \beta_n$. The likelihood function can be defined as follows:

$$L(\vec{\beta}, \beta_0) = \prod_{i=1}^{m} p(\vec{x}_i)^{y_i} (1 - p(\vec{x}_i))^{1 - y_i} \quad (4)$$

where $\vec{\beta}$ is equal to $\{\beta_1 \ldots \beta_n\}$, $\vec{x}$ is equal to $\{x_1 \ldots x_n\}$, m is equal to the number of records in the training data set, and y is the true in-hospital mortality or survival.

The training data set includes a plurality of records, each corresponding to an ICU patient. The record for an ICU patient includes one or more measurements over time, typically a plurality of measurements over time (i.e., a time series), for each variable of the mortality log R model 52. Typically, the measurements span from admittance to the ICU until the patient dies or is discharged from the ICU, whichever comes first, or until a predetermined period of time (e.g., 48 hours) passes or the patient dies, whichever comes first. Further, the record for a patient includes an indication as to whether the patient died before discharge from the ICU or lived to be discharged from the ICU. As above, the training population of the training data set can be localized to a patient population to which the patient being assessed by the mortality log R model 52 belongs. For example, the training population can be localized to a patient population sharing a disease or physiological condition with the patient, a patient population corresponding to a medical institution treating the patient, a patient population corresponding to a geographical region (e.g., a country, a state, a city, a county, etc.) of the patient, or a combination of the foregoing patient populations.

PhysionNet/CinC Challenge 2012 made a data set describing eight thousand ICU patients publicly available to develop methods for patient-specific prediction of in-hospital mortality. The data set contains measurements for up to 42 variables for each ICU patient. The variables include general descriptors (e.g., age, gender, height, weight, etc.), vital signs and lab tests. For each patient, each variable includes a single measurement/value (e.g., for a general descriptor) or a time series of measurements spanning from the first ICU stay of the patient for a period of 48 hours (unless the patient died before then) with at least one measurement within the 48 hour period and vital signs and lab tests measured every hour. Further, the data set contains the mortality outcome for half of these ICU patients. While not necessary, $\beta_0 \ldots \beta_n$, can be determined using the data set provided by PhysionNet/CinC Challenge 2012 as the training data set.

During application of the mortality log R model 52, measurements of predictor variables are applied to the definition of the mortality log R model 52, described by Equation (3). Each variable is measured in response to an event (e.g., a periodic event (e.g., every 10 minutes), a physiological event (e.g., atrial fibrillation), a clinical event (e.g., check-in to the ICU), etc.). Each time at least one predictor variable of the patient is measured, or in response to some other event (e.g., a periodic event, a physiological event, etc.), the mortality log R model 52 updates the prediction using the most recent measurements.

Suitably, the predictor variables are selected by a clinical expert using their years of experience and/or a trial and error approach to find the set of variables that best predicts mortality. Further, the selected variables can be specifically selected for the patient to which the mortality HMM 12 is being applied. As illustrated, the mortality log R model 52 predicts the risk of mortality using a demographic variable 54 (i.e., age), cardio-pulmonary variables 56 (i.e., PF ratio and HR-Diastolic BP(interaction)), renal variables 58 (i.e., creatinine and BUN), a hepatic variable 60 (i.e., bilirubin), a neurological assessment variable 62 (i.e., GCS), a diabetes variable 64 (i.e., glucose), disease development variables 66 (i.e., sepsis and pneumonia), and a mortality-prediction variable 68 (i.e., a mortality prediction from the mortality HMM 12).

To validate the mortality log R model 52, both the mortality log R model 52 and the SAPS-I model were tested using a subset of the data provided by the PhysionNet/CinC Challenge 2012. 4,000 patient records were selected at random, of which 554 died in-hospital and 3,446 survived. Patients under the age of 16 and patients whose initial ICU stays were shorter than 48 hours (i.e., approximately the median stay) were excluded from the random selection.

Figure 8:
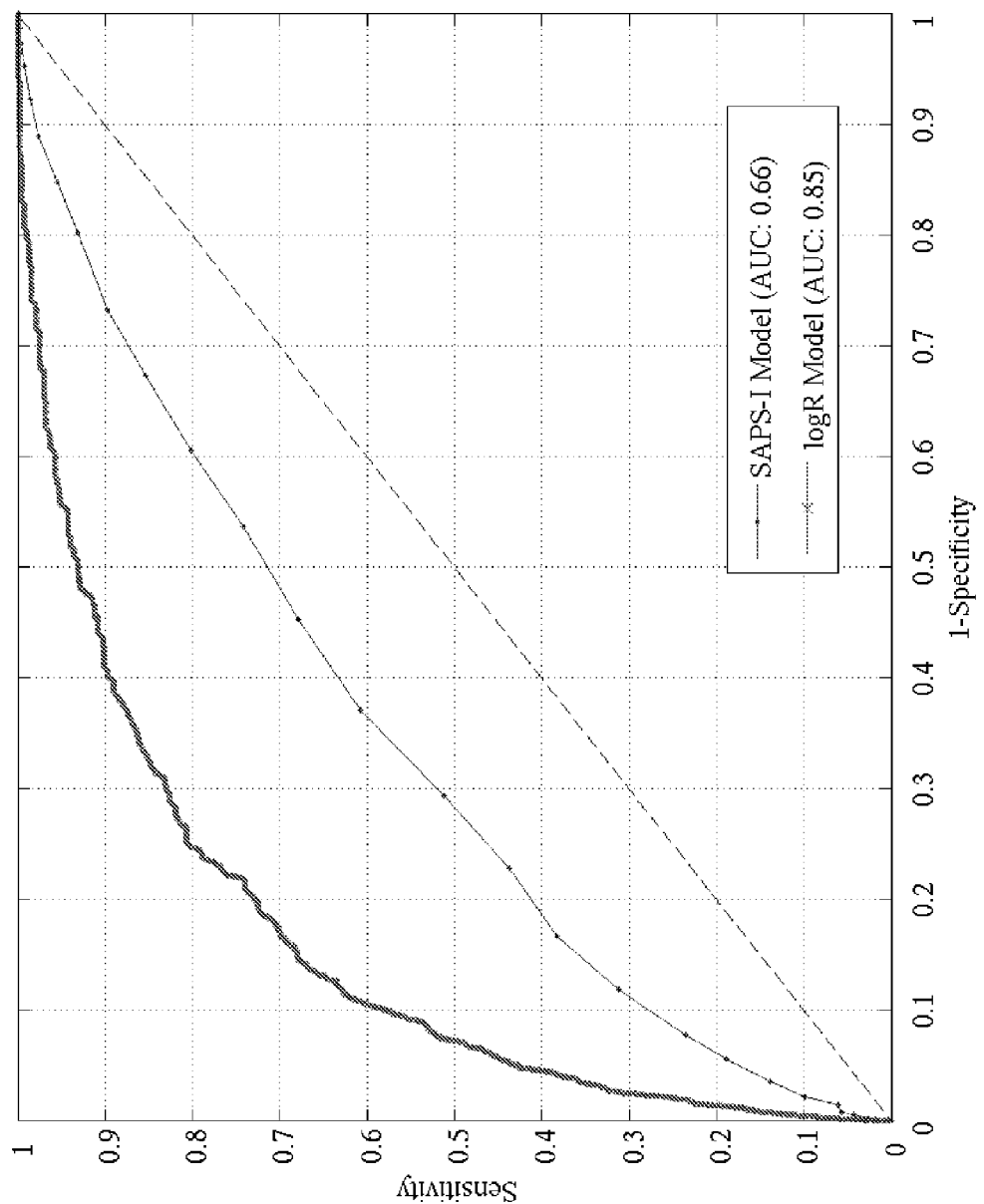
FIG. 8 illustrates ROC curves for both a mortality log R model and a SAPS-I model.

ROC analysis was performed on the selected records using the mortality log R model 52 and the SAPS-I model to assess the detection capability of the mortality log R model 52. In that regard, two metrics, the AUC and the minimum of sensitivity and PPV, were obtained from the ROC curves to evaluate the detection capability of the mortality log R model 52. With these metrics, the higher the value is (i.e., the closer to 1), the better the detection capability. With reference to FIGS. 8 and 9, results of the ROC analysis are shown. FIG. 8 illustrates the ROC curves for both the mortality log R model 52 and the SAPS-I model. FIG. 9 illustrates a table showing both the AUC and the minimum of sensitivity and PPV for both the mortality log R model 52 and the SAPS-I model. As can be seen, the AUC of the mortality log R model 52 is 85%, whereas the AUC for the SAPS-I model is 66%. Further, the minimum of sensitivity and PPV of the mortality log R model 52 is 52%, whereas the minimum of sensitivity and PPV for the SAPS-I model is 31.7%. Hence, the detection capability of the mortality log R model 52 exceeds that of the SAPS-I model.

A Hosmer-Lemeshow (H statistic) goodness of fit test was performed to assess the predictive capability of the mortality log R model 52. To perform the test, are observations are grouped based on the expected probabilities (i.e., risk). For example, the observations are sorted in increasing order of their estimated event probability. The observations are then divided into G groups. After grouping the observations, the hypothesis that the difference between observed and expected events is simultaneously zero for all the groups is tested to obtained the H-statistic. This is performed by calculating the Pearson chi-square statistic from the 2×G table (i.e., 2 rows and G columns, or vice versa) of observed and expected frequencies for the G groups.

The H-statistic for the case of a simple random sample is defined as:

$$H = \sum_{g=1}^{G} \frac{(O_g - N_g \bar{\pi}_g)^2}{N_g \bar{\pi}_g (1 - \bar{\pi}_g)} \quad (5)$$

where N is the total frequency of subjects in a group, O is the total frequency of event outcomes in a group, and $\bar{\pi}$ is the average estimated probability of an event outcome for a group. The subscript of these variables indicates the group. The distribution of the H statistic is approximated by a chi-square with (G-2) degrees of freedom.

With reference to FIG. 9, the illustrated table further shows H statistic for both the mortality log R model 52 and the SAPS-I model. As can be seen, the H statistic of the mortality log R model 52 is 26.90, whereas the H statistic for SAPS-I model is 66.04. With the H statistic, the lower the value is (i.e., the closer to 0), the better the prediction capability. Hence, the mortality log R model 52 outperformed the SAPS-I.

As described above, the mortality HMM 12 and the mortality log R model 52 provide valuable tools to clinicians. For example, these models could be: 1) applied in the ICU to detect and predict patients' mortality; 2) integrated with other existing clinical decision support (CDS) solutions in the ICU; 3) embedded as part of an ICU patient monitor and used by critical care physicians; 4) used for continuous monitoring of mortality or any critical illness development; 5) used to generate trend based alarms for mortality risk of critically ill patients due to the dynamic nature of the mortality HMM 12; 6) integrated with an intervention regime or protocol for ICU patients using the risk inferred by the mortality HMM 12; or 7) targeted to only evaluate the mortality risk for a critically ill patient due to a particular organ failure using measurements from the relevant variables only.

While the mortality HMM 12 and the mortality log R model 52 were used to predict mortality, these models could also be used to detect other physiological conditions, such as acute kidney injury (AKI) and disseminated intravascular coagulation (DIC), by using different sets of observed/predictive variables (e.g., variables describing drugs, vital signs and/or medications). Further, the mortality log R model 52 could use a linear discriminant analysis model instead of a logistic regression model with the same or different sets of predictive variables for the prediction of mortality or any other acute illness. Even more, the mortality HMM 12 and the mortality log R model 52 can be used as inputs for each other. For example, the mortality HMM 12 can serve as a predictive variable of the mortality log R model 52, or the mortality log R model 52 can serve as an observed variable of the mortality HMM 12. Moreover, the patient data collected through application of the mortality HMM 12 and/or the mortality log R model 52 can be used to retrain the models (i.e., a feedback loop can be developed).

Figure 10:
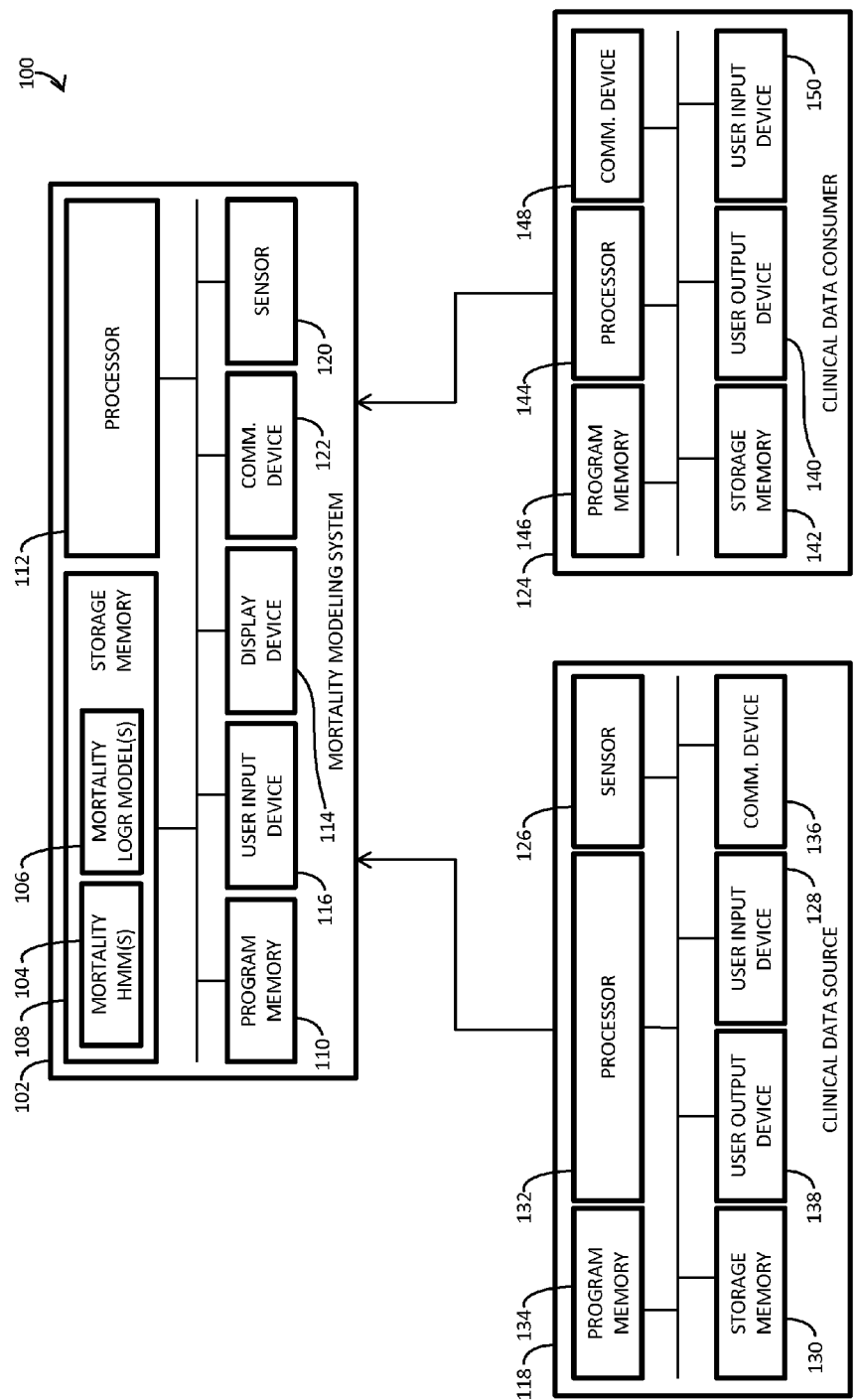
FIG. 10 illustrates a medical system for predicting the risk of mortality.

With reference to FIG. 10, a medical system 100 for predicting the risk of mortality is illustrated. The medical system 100 includes a mortality modeling system 102 that can generate and/or train mortality models, such as mortality HMMs 104 (e.g., as described above) and mortality log R models 106 (e.g., as described above), to predict the risk of patient mortality, and/or use the mortality models 104, 106 (as trained) to predict the risk of patient mortality. The mortality models 104, 106 are suitably stored in at least one storage memory 108 of the mortality modeling system 102. Further, the requisite logic to generate, train and/or use the mortality models 104, 106 is suitably implemented as processor executable instructions stored on at least one program memory 110 of the mortality modeling system 102 and executed by at least one processor 112 of the mortality modeling system 102.

A graphical user interface (GUI) can be used to allow users of the mortality modeling system 102 to interact with the mortality modeling system 102. A display device 114 of the mortality modeling system 102 can display a plurality of graphical elements to users that the users can interact with using a user input device 116 of the mortality modeling system 102. Manipulation of these graphical elements then allows the users to control aspects of the mortality modeling system 102, such as the generation and the training of the mortality models 104, 106.

The mortality models 104, 106 can be generated and trained using clinical data received from one or more remote clinical data sources 118 or locally from the storage memory 108, a sensor 120, or the user input device 116, of the mortality modeling system 102. For example, the storage memory 108 can include the PhysioNet/CinC Challenge 2012 data, discussed above. As another example, a clinician can specify model parameters (e.g., $\beta_0 \ldots \beta_n$) and/or select model variables (e.g., HR) using the user input device 116. Communication with remote clinical data sources is suitably performed using a communication device 122 of the mortality modeling system 102. Generating a mortality model includes selecting the predictive/observed variables to be used by the model. Training a mortality log R model includes determining the constant $\beta_0$, as well as the coefficients $\beta_1 \ldots, \beta_n$ for the predictive variables. Training a mortality HMM includes determining the transition probabilities and the probabilities of the predictive observed variables.

Although not necessary, the mortality models 104, 106 can be generated and/or trained for specific patients. For example, the predictive/observed variables used by a mortality model can be specifically selected for the patient using the model. As another example, a mortality model can be trained using training data describing a patient population to which the patient being assessed by the model belongs.

Mortality risks can be predicted for individual patients (e.g., ICU patients) using the mortality models 104, 106 (as trained) corresponding to the patients, as well as clinical data corresponding to the patients. The mortality models 104 can be generated and trained using the mortality modeling system 102 or some other system. Further, the clinical data can be received from the remote clinical data sources or locally from the storage memory 106, a sensor (not shown), or the user input device 114, of the mortality modeling system 102. The clinical data for a patient includes measurements for the predictive/observed variables of the model corresponding to the patient and other relevant data. The measurements are typically received over time to track the trend of the corresponding predictive/observed variables. Where measurements are received over time, the mortality risk is typically continuously updated as new measurements become available.

The mortality risks determined for individual patients can be monitored for alarm conditions to generate alarms. For example, the determined mortality risks can be compared to thresholds to generate an alarm in response to a mortality risk exceeding a threshold. The alarm conditions can be patient-specific, and automatically or manually determined. Further, more sophisticated alarming conditions than thresholds can be employed. Alarms can be locally generated (e.g., using the display device 114 of the mortality modeling system 102) or remotely generated by notifying a remote, clinical data consumer 124 of the alarm condition. For example, a visual or audio representation of the alarm can be locally or remotely generated.

The medical system 100 can include one or more clinical data sources 118 remote from the mortality modeling system 102. A clinical data source 118 is any source of clinical data for the mortality modeling system 102. Examples of clinical data sources include, but are not limited to, patient monitors, nursing stations, mobile communications devices, patient information systems, clinical decision systems, and so on.

A clinical data source 118 can generate clinical data describing measurements of predictive/observed variables (e.g., physiological parameters, such as HR, or lab tests, such as creatinine) using a sensor 126 of the clinical data source 118. A clinical data source 118 can also generate clinical data through analysis and/or processing of other clinical data. For example, a clinical data source 118 can compute a SAPS-I score. Further, a clinical data source 118 can receive clinical data (e.g., a measurement of a predictive/observed variable) from a user input device 128 of the clinical data sources 118. Examples of such clinical data include measurements of level of consciousness. Even more, a clinical data source 118 can store clinical data obtained locally (e.g., from a user input devices 128 of the clinical data source 118), or from a system or device of the medical system 100 remote from the clinical data source 118, on at least one storage memory 130 of the clinical data source 118.

Each of the clinical data sources 118 typically includes at least one processor 132 and at least one program memory 134. The program memory 134 includes processor executable implementing the functionality of the clinical data source 118, and the processor 132 executes the processor executable instructions. Further, each of the clinical data sources 118 further includes a communication device 136 allowing the clinical data source 118 to provide the mortality modeling system 102 with clinical data. Optionally, a clinical data source 118 can include a user output device 138 displaying graphical elements that can be manipulated using a user input device 128 of the clinical data source 118 to control aspects of the clinical data source 118.

The medical system 100 can also include one or more clinical data consumers 124. The clinical data consumers 124 are remote from the mortality modeling system 102 and receive mortality alarms and/or mortality risk predictions from the mortality modeling system 102. The clinical data consumers 124 can use the mortality alarms or mortality risk predictions for any number of tasks. For example, a clinical data consumer 124 can display or otherwise present (e.g., via audio) mortality alarms and/or risk predictions to clinicians using a user output device 140 of the clinical data consumer 124. As another example, a clinical data consumer 124 can store mortality alarms and/or risk predictions on at least one storage memory 142 of the clinical data consumer 124. As another example, a clinical data consumer 124 can monitor the mortality risk predictions to generate alarms, which can be presented to clinicians using a user output device 140 of the clinical data consumer 124. Examples of clinical data consumers include patient monitors, nursing stations, mobile communications devices, patient information systems, clinical decision systems, and so on.

Each of the clinical data consumers 124 typically includes at least one processor 144 and at least one program memory 146. The program memory 146 includes processor executable implementing the functionality of the clinical data consumer 124, and the processor 144 executes the processor executable instructions. Further, each of the clinical data consumers 124 further includes a communication device 148 allowing the clinical data consumer 124 to receive mortality alarms and/or mortality risk predictions from the mortality modeling system 102. Optionally, a clinical data consumer 124 can include a user output device 140 displaying graphical elements that can be manipulated using a user input device 150 of the clinical data consumer 124 to control aspects of the clinical data consumer 124.

While the functionality of the medical system 100 was described as being implemented by a combination of processors and program memories, the processors executing external instructions on the corresponding program memories, it is to be appreciated that at least some of the functionality can be implemented in hardware without the use of a programmable processor. For example, the functionality of the medical system 100 can be implemented in an application-specific integrated circuit (ASIC) or a field-programmable gate array (FPGA). Further, notwithstanding that the mortality modeling system 102 was directed towards the predicting the risk of mortality, the mortality modeling system can be used to model other physiological conditions, such as AKI.

As used herein, the term measurement is used to mean determining a present value. Hence, measuring a variable means determining the present value of the variable. Further, as used herein, a memory includes one or more of: a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; and the like. Even more, as used herein, a processor includes one or more of a microprocessor, a microcontroller, a graphic processing unit (GPU), and the like; a controller includes at least one memory and at least one processor, the processor executing processor executable instructions on the memory, or includes specialized hardware implementing a method; a user input device includes one or more of a mouse, a keyboard, a touch screen display, one or more buttons, one or more switches, one or more toggles, and the like; a user output device includes one or more of a display device, and auditory device, and so on; and a display device includes one or more of a liquid crystal display (LCD) display, an light emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A medical modeling system for predicting a risk of a physiological condition for a patient, said medical modeling system comprising:
at least one processor programmed to:
receive measurements of a plurality of predictive variables for the patient, the plurality of predictive variables predictive of the risk of the physiological condition;
calculate the risk of the physiological condition by applying the received measurements to at least one model modeling the risk of the physiological condition using the plurality of predictive variables, the calculating including:
receiving a time series of measurements for a predictive variable of the plurality of predictive variables;
calculating a predicted risk of the physiological condition by applying the received times series of measurements to a hidden Markov model modeling the risk of the physiological condition; and
calculating the risk of the physiological condition by applying the received measurements and the calculated predicted risk to a logistic regression model modeling the risk of the physiological condition;
output an indication of the risk of the physiological condition to a clinician;
train at least one of the hidden Markov model and the logistic regression model based on a training population before calculating the risk of the physiological condition;
retrain the at least one of the hidden Markov model and the logistic regression model based on the received measurements and an outcome describing whether the physiological condition occurred in the patient; and
calculate the risk of the physiological condition for another patient using the retrained model;
a clinical decision system programmed to:
receive the calculated risk of the physiological condition;
provide a clinician with clinical decision support based on the calculated risk of the physiological condition;
monitor the calculated risk of the physiological condition for an alarm condition; and
in response to the alarm condition, control an alarm output unit to output an alarm indicative of the physiological condition to the clinician.

2. The medical modeling system according to claim 1, wherein the physiological condition is mortality.

3. The medical modeling system according to claim 1, wherein the at least one processor is further programmed to:
receive the measurements of the plurality of predictive variables over time; and
continuously calculate the risk of the physiological condition.

4. The medical modeling system according to claim 1, wherein the at least one processor is further programmed to:
train the model based on a training population specifically selected for the patient.

5. The medical modeling system according to claim 1, wherein the at least one processor is further programmed to:
select the plurality of predictive variables specifically for the patient; and
generate a model of the at least one model using the selected plurality of predictive variables.

6. The medical modeling system according to claim 1, wherein the at least one processor is further programmed to:
select the plurality of predictive variables to include at least one variable for observing each of: oxygen transport, ventilation, and perfusion; organ dysfunction other than liver dysfunction; and liver dysfunction.

7. A medical modeling method for predicting a risk of a physiological condition for a patient, said medical modeling method comprising:
receiving measurements of a plurality of predictive variables for the patient, the plurality of predictive variables predictive of the risk of the physiological condition;
calculating the risk of the physiological condition by applying the received measurements to at least one model modeling the risk of the physiological condition using the plurality of predictive variables, the calculating including:
receiving a time series of measurements for a predictive variable of the plurality of predictive variables;
calculating a predicted risk of the physiological condition by applying the received time series of measurements to a hidden Markov model modeling the risk of the physiological condition; and
calculating the risk of the physiological condition by applying the received measurements and the calculated predicted risk to a logistic regression model modeling the risk of the physiological condition;
outputting an indication of the risk of the physiological condition to a clinician;
training at least one of the hidden Markov model and the logistic regression model based on a training population before calculating the risk of the physiological condition;
retraining the at least one of the hidden Markov model and the logistic regression model based on the received measurements and an outcome describing whether the physiological condition occurred in the patient,
calculating the risk of the physiological condition for another patient using the retrained model; and
with a clinical decision system:
receive the calculated risk of the physiological condition;
provide a clinician with clinical decision support based on the calculated risk of the physiological condition;
monitoring the calculated risk of the physiological condition for an alarm condition; and
in response to the alarm condition, controlling an alarm output unit to output an alarm indicative of the physiological condition to the clinician.

8. The medical modeling method according to claim 7, wherein the physiological condition is mortality.

9. The medical modeling method according to claim 7, further including:
selecting the plurality of predictive variables to include least one variable for observing each of: oxygen transport, ventilation, and perfusion; organ dysfunction other than liver dysfunction; and liver dysfunction.

10. At least one processor configured to perform the method according to claim 7.

11. A non-transitory computer readable medium carrying software which controls one or more processors to perform the method according to claim 7.

12. A medical system comprising:
a medical modeling system for predicting a risk of a physiological condition for a patient, the medical modeling system configured to:
  receive measurements of a plurality of predictive variables for the patient, the plurality of predictive variables predictive of the risk of the physiological condition; and
  train at least one of a hidden Markov model and a logistic regression model based on a training population;
  calculate the risk of the physiological condition by applying the received measurements to at least one model modeling the risk of the physiological condition using the plurality of predictive variables, the at least one model including at least one of the hidden Markov model and a logistic regression model, the calculating including:
  receive a time series of measurements for a predictive variable of the plurality of predictive variables:
    calculating a predicted risk of the physiological condition by applying the received measurements to the hidden Markov model modeling the risk of the physiological condition; and
    calculating the risk of the physiological condition by applying the received measurements and the calculated predicted risk to the logistic regression model modeling the risk of the physiological condition;
  retrain the model based on the received measurements and an outcome describing whether the physiological condition occurred in the patient; and
  calculate the risk of the physiological condition for another patient using the retrained model; and
a clinical decision system configured to:
  receive the calculated risk of the physiological condition;
  provide a clinician with clinical decision support based on the calculated risk of the physiological condition;
  monitor the calculated risk of the physiological condition for an alarm condition; and
  in response to the alarm condition, control an alarm output unit to output an alarm indicative of the physiological condition to the clinician.

13. The medical system according to claim 12, wherein the medical modeling system is further configured to:
  select the plurality of predictive variables to include least one variable for observing each of: oxygen transport, ventilation, and perfusion; organ dysfunction other than liver dysfunction; and liver dysfunction.

\* \* \* \* \*